Figure 1:
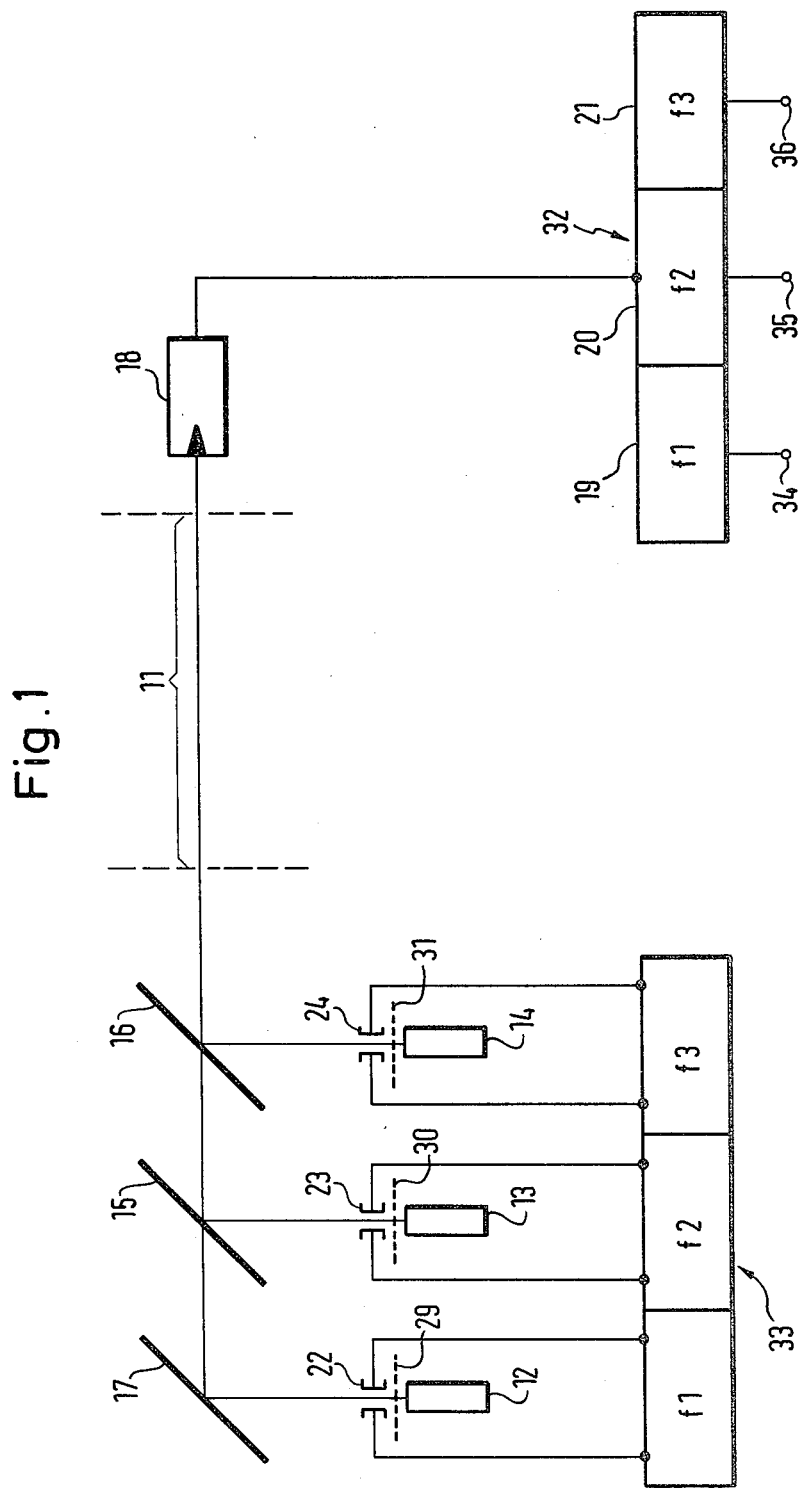

United States Patent [19]

Roess et al.

[11] 4,383,181
[45] May 10, 1983

[54] METHOD AND APPARATUS FOR ANALYZING A GASEOUS MIXTURE

[75] Inventors: Dieter Roess, Planegg; Wolfgang Hartig, Essen, both of Fed. Rep. of Germany

[73] Assignee: Erwin Sick GmbH Optik-Elektronik, Fed. Rep. of Germany

[21] Appl. No.: 212,660

[22] Filed: Dec. 3, 1980

[30] Foreign Application Priority Data

Dec. 3, 1979 [DE] Fed. Rep. of Germany ....... 2948590

[51] Int. Cl.$^3$ ............................................ G01N 15/06
[52] U.S. Cl. .................................... 250/573; 250/226; 356/320
[58] Field of Search ............... 250/339, 344, 345, 573, 250/226; 356/320, 407, 330

[56] References Cited

U.S. PATENT DOCUMENTS

| | | | |
|---|---|---|---|
| 3,151,247 | 9/1964 | Auvermann | 356/320 |
| 3,819,945 | 6/1974 | Egan et al. | 356/330 |
| 3,820,901 | 6/1974 | Kreuzer | 250/345 |
| 3,994,590 | 11/1976 | Di Martini et al. | 356/407 |
| 4,193,691 | 3/1980 | Fjarlie | 356/330 |

Primary Examiner—David C. Nelms
Attorney, Agent, or Firm—Townsend and Townsend

[57] ABSTRACT

A gaseous mixture containing a number of molecular gases is analyzed to establish the amount of each individual gas by directing a light beam along a measurement path 11 through the gas. Each of the spectral component is selected to coincide with a respective vibrational-rotational-excitation band of one of the gases. The attenuation produced in each of the spectral components in its passage along the measurement path 11 serves as an indication of the concentration of the associated gas. The spectral components are generated either from distinct light sources 12, 13, 14 or are alternatively produced by spectral division of light from a multiple line or broad band source. Different marking frequencies f1, f2 and f3 are used to modulate each of the spectral components so that the signal received from the single photoelectric receiver 18 can be subsequently demodulated by three demodulators 19, 20, 21 to recover information relating to the individual spectral components. A series of reference beams at spectral frequencies which are unattenuated by the gases present in the measurement section are used for comparison purposes and allow factors such as contamination of the optics and ageing of the light source to be taken into account. A number of different embodiments are disclosed showing various ways of generating the spectral measurement and reference components and of processing the signals delivered by the single photoelectric receiver 18.

8 Claims, 6 Drawing Figures

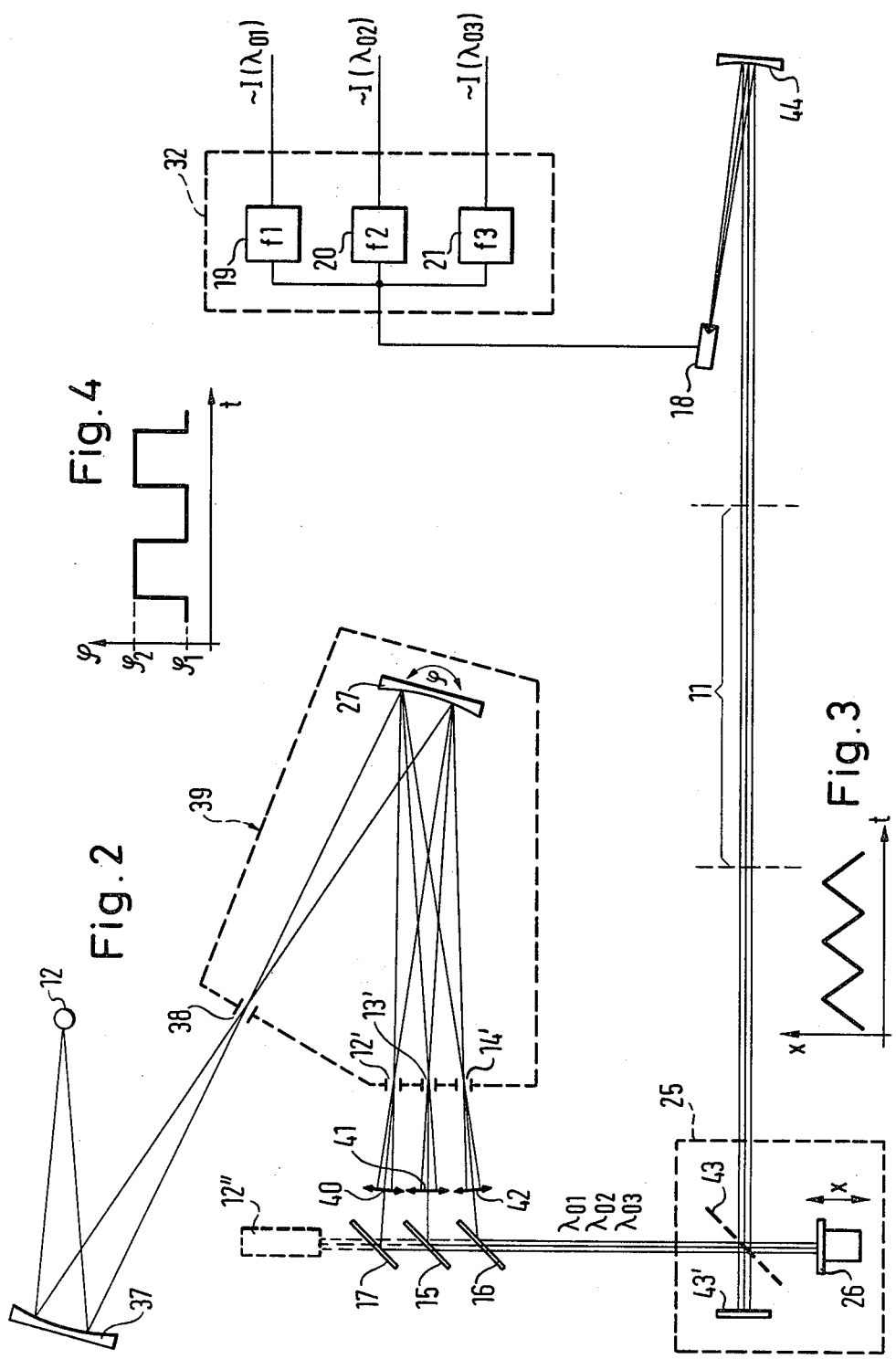

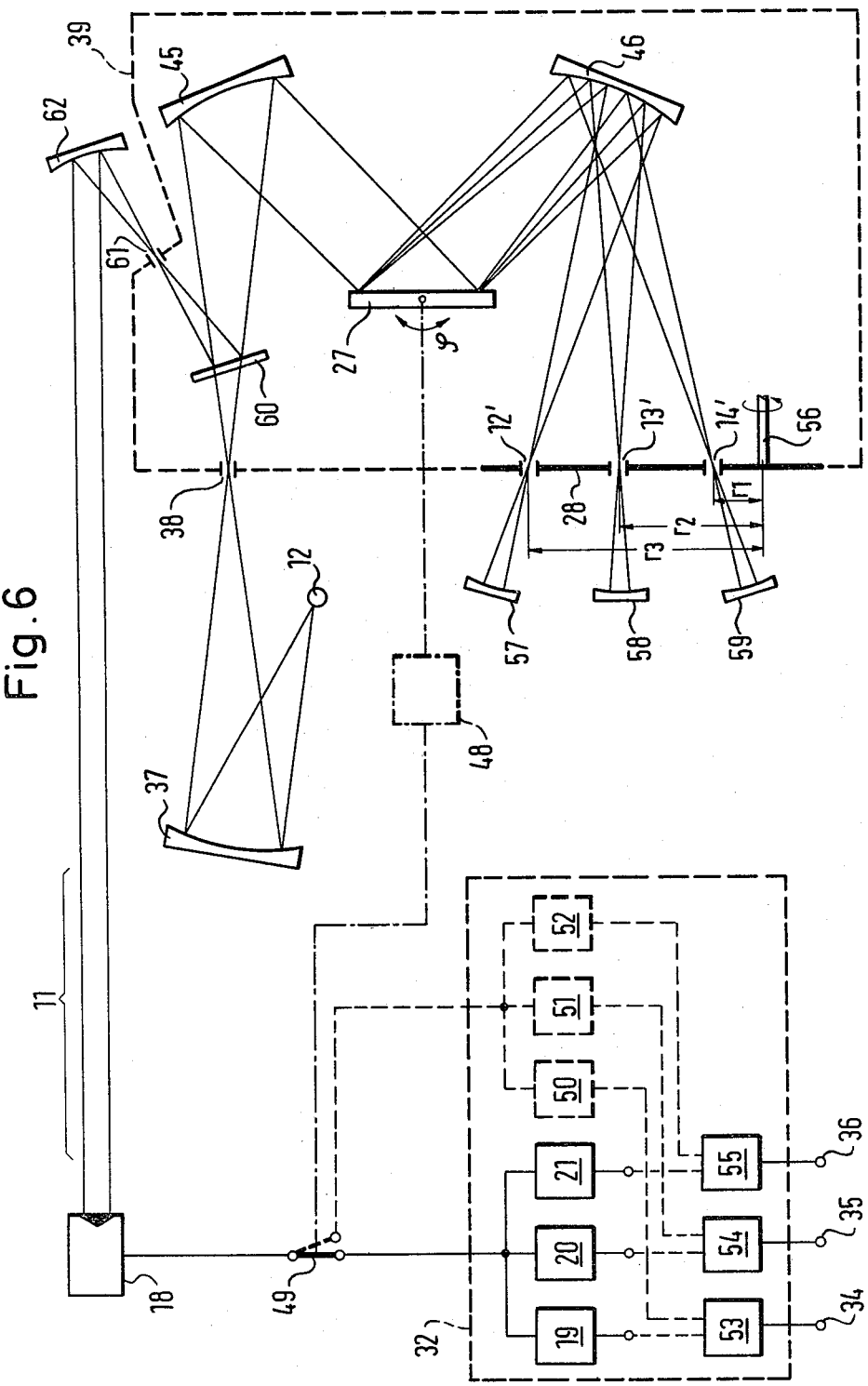

METHOD AND APPARATUS FOR ANALYZING A GASEOUS MIXTURE

The invention relates to a method and to an apparatus for analysing the gases of a gaseous mixture containing several molecular gases and has particular reference to an arrangement wherein the absorption of spectral components characteristic of respective vibrational-rotation-excitation bands of each of the gases to be analysed is measured by means of electromagnetic radiation which contains these spectral components and which is passed through a measuring section arranged in the gaseous mixture. The content of the gas associated with each spectral component is determined from the measured absorption.

In known apparatus and methods of this kind for analysing gases the individual spectral components have to be serially measured, i.e. measured one after the other, which requires complex equipment. The known fully equipped Fourier spectrometers have a complex and expensive construction. They also require complicated and highly developed electronic processing circuitry.

In contrast the principal object underlying the present invention is to provide a method and an apparatus for analysing gases in which the presence and proportions of several gas components can be measured in parallel, i.e. at the same time, without the need for excessively complicated equipment and electronic processing circuitry.

In order to accomplish this task the invention envisages a method wherein each of the spectral components which is characteristic of a respective one of the gases is modulated by a marking frequency which is uniquely associated therewith and wherein, after the passage through the measuring section, the individual spectral components are filtered out of the radiation, which contains all the required spectral components, in dependence on their marking frequencies and are used for the analysis of the gases.

The invention thus uses a kind of frequency division multiplex technology for processing information. In this way it is possible to simultaneously investigate and quantitatively evaluate the absorption of spectral components of the vibrational-rotational-excitation bands of several molecular gases such as CO, $SO_2$, and $NO_x$. This can be done on the spot, for example in a chimney or flue, or in a measuring cell which is filled with the gas to be investigated. The measurements which can be made using the method of gas analysis proposed by the invention are free of cross-sensitivity with regard for example to dust and water vapour.

It is particularly advantageous if one or more spectral reference components which lie outside of the vibrational-rotational-excitation bands of all the gases contained in the mixture are transmitted through the measurement section and are used as reference values for the measured values. The invention thus preferably makes use of differential absorption whereby changes in intensity as a result of ageing of the light source and contamination of the optical components are automatically eliminated.

A simple apparatus for carrying out the method of the invention is characterized by an arrangement in which several light sources, each of which supplies one of the characteristic spectral components and the radiation of each of which is modulated by a marking frequency, are connected to the measuring section and irradiate a common photoelectric receiver, with electronic filters, each of which is tuned to a respective one of the marking frequencies, being connected after the photoelectric receiver.

The measurement section, which can be formed by a chimney or a gas cell, is thus permeated with radiation containing several distinct and differently modulated spectral components. Each individual spectral component is attenuated in proportion to the concentration of the associated gas which is under investigation. The photoelectric receiver can, for example, take the form of an infra-red detector on which the radiation is focussed. The measurement path through the measurement section can be increased by using a retro-reflector and multiple crossings of the measurement section in order to raise the sensitivity of the measurement.

The analysis of the signals delivered from the photoelectric receiver takes place via a simple electronic processing circuit which is constructed as a low frequency spectral analyser. The electronic processing essentially consists of a series of narrow band filters which are accurately tuned to respective ones of the individual marking frequencies. By way of example three marking frequencies are preferably used to analyse three gas components. The integrated signal at the output of each filter is proportional to the intensity of the individual spectral components at the photoelectric receiver. The spectral analyser can be realized in particularly simple electronic form by a series of active filters. The resolution of the analyser should have an order of magnitude $$\Delta f // f = 10^{-3}$$

in order to achieve an acceptable accuracy of measurement.

This resolution can be achieved by a series of synchronous detectors with subsequent integration. In accordance with the invention it is the band width of the filter that determines the spectral resolution and not for example the band width of the individual light sources.

In place of several light sources each supplying a specific spectral component one can also use broad band light sources with narrow band filters, in particular interference filters, arranged in front of these light sources. Each light source must, however, then contain the spectral component which is filtered out by the associated filter.

The light sources are usefully connected to the measuring section via beam dividers and, if required, a deflecting mirror.

In order to modulate the spectral components at the desired marking frequencies respective appropriately controlled optical modulators can be inserted between the light source by the beam dividers and, if provided, the deflecting mirror. It is however also possible for the light sources themselves to be modulated.

In a particularly preferred embodiment an interferometer having a reflecting mirror which is displaceable to and fro at a predetermined speed over at least a few wavelengths, is inserted between, on the one hand, the beam dividers and, if provided, the deflecting mirror and, on the other hand, the measuring section. A Michelson-interferometer is, by way of example, particularly suited to this purpose.

The speed at which the reflecting mirror is periodically moved to and fro is usefully constant. The electronic processing circuit should usefully be scanned in the dark regions at the reversal points of the movement. The interferometer operates, in accordance with the invention as a very exact modulator for the individual spectral components. A single light source which supplies radiation with all the required spectral components can be provided in place of several light sources and the associated beam dividers and, if provided, the associated deflecting mirror. For this purpose one can for example use a multiple line laser which transmits radiation containing the required spectral components and which is particularly preferred for the purposes of the present invention. The light sources can also be secondary light sources which are formed by spectral division of radiation containing all the required spectral components. The spectral division usefully take place at a reflection grating which is followed by a series of slots with a respective spectral component being concentrated in each of the slots. Spectral division apparatus of this kind is also termed a polychromator. A polychromator can in particular take the form of a reflection grating used in the so-called Ebert arrangement, or a holographic concave grating, both of which are able to select narrow band spectral zones arranged around specific basic wave lengths from a continuous spectrum, in particular from an infra-red light source. The outlet slots of the polychromator are so adjusted that the radiation which is selected overlaps with disjoint regions of the absorption bands of the gases under investigation. The task of the polychromator is only to produce a coarse initial spectral selection. The polychromator is thus constructed to provide the maximum light intensity.

The same result can be achieved by using interference filters or gradient density filters with collimated light beams which are generated by splitting up a light beam leaving a light source by means of beam dividers. The polychromator can be omitted when using an infra-red laser with a multiple line spectrum as mentioned above.

A particularly simple embodiment of the invention features an arrangement in which the slots are each able to execute a periodic modulating movement at the associated marking frequencies. It is particularly preferred for all the slots to be disposed in a multiply repeating arrangement at different radii of a rotating aperture disk. Although the above-mentioned interferometer is particularly useful in the first instance in the infra-red spectral range it can also be used to great advantage with an embodiment in which the slots execute a modulating movement and gases with wide absorption lines are to be detected, for example larger inorganic molecules CO (IR), $SO_2$ (UV) and $NO_2$ (VIS). The use of an interferometer is also sensible in situations where a light source with several individual lines can be utilized.

The apertured disk preferably has a series of slots arranged on circular arcs of the disk at different radii with mark to space ratios of 1:1. Each series of slots is associated with one of the spectral components selected by the polychromator. The different marking frequencies for each of the spectral components are readily achieved by varying the number of slots in each series. It will be understood that the modulation frequencies are determined by the number of slots in each series and the speed of rotation of the apertured disk.

In order periodically to obtain a respective reference value for each of the measured values the reflection grating can be periodically pivoted between two positions whereby, in one position, the spectral measuring components are generated at the slots and, in the other position, the spectral reference components are generated at the slots.

In this manner the apparatus of the invention is modified to form a differential spectrometer. It is important that the reference wavelengths selected at the outlet slots do not coincide with the spectral components of the gases under investigation. This also applies to the alternative arrangement in which interference or gradient density filters are used. In each case new marking frequencies are associated, in accordance with the invention, with the spectral reference components. These marking frequencies can then be analysed during signal processing by switching over to a second set of filters corresponding to these frequencies at the same time as the position of the grating is changed.

A simple logic circuit connected after the filters is able to calculate the normalized concentration of each of the relevant gases. The normalized concentration is independent of transmission losses due to contamination of the optical components, ageing of lamps, and absorption by other gases that are present (such as water vapour), provided these gases, the concentration of which is not to be measured, exhibit the same absorption behaviour at both the measurement wavelength and also the reference wavelength.

The significant advantages of the method and apparatus of the present invention stem from the fact that several gas components can be measured in parallel and that differential measurement is also possible. As a result the method and the apparatus of the invention have no cross-sensitivity with regard to dust, water vapour and intensity losses. When compared with a full Fourier-spectrometer the spectrometer of the invention requires only a simple and economical electronic processing circuit. The complexity of the two beam interferometer which is usefully used in connection with the invention is significantly reduced. It is not necessary to measure the change in the path difference it is merely necessary for the path difference to remain constant.

Figure 5:
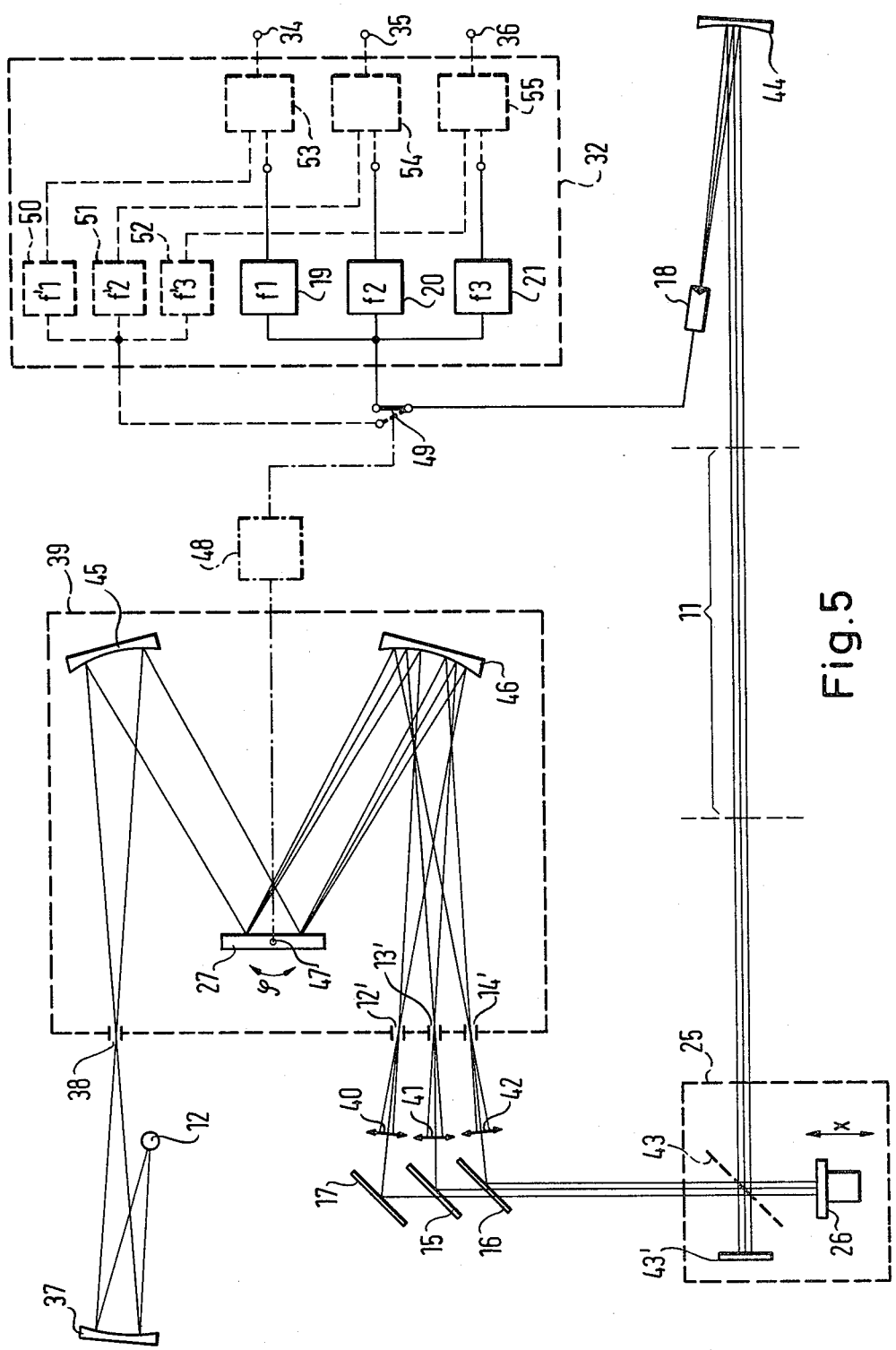

The invention will now be described in more detail in the following by way of example only and with reference to the accompanying drawings in which are shown:

FIG. 1 a schematic block circuit diagram of a simple basic embodiment of an apparatus for analysing gases and constructed in accordance with the invention, FIG. 2 a schematic view of an embodiment operating with a two beam interferometer, FIG. 3 a travel versus time diagram showing the movement of one of the mirrors incorporated in the two beam interferometer of FIG. 2, FIG. 4 an angle versus time diagram showing the angular movement of a reflection grating used in connection with the embodiment of FIG. 2, FIG. 5 an analogous view to that of FIG. 2 but showing a further advantageous embodiment and FIG. 6 a schematic side view of a simplified embodiment of an apparatus in accordance with the invention for analysing gases.

In FIGS. 1, 2, 5 and 6 the electronic components are illustrated in the form of block diagrams.

Referring firstly to FIG. 1 there can be seen three light sources 12, 13, 14 which can for example be lasers and which are arranged alongside each other. Each light source emits a light wave with a quite specific frequency. These light waves will be referred to in the following as spectral components. The spectral components can also be generated by arranging highly selective optical filters 29, 30 and 31 in front of the light sources 12, 13 and 14 respectively.

The light emitted from the light sources 12, 13, 14 passes via the filters 29, 30, 31 and optical modulators 22, 23, 24 to a deflecting mirror 17 and beam dividers 15, 16 respectively which deflect the light beams from the individual light sources and unite them into a single light beam passing through a measurement section 11 to a photodetector 18. The photodetector 18 is connected to an electronic processing circuit 32 which contains narrow band frequency filters 19, 20 and 21. The filters are tuned to those frequencies f1, f2 and f3 with which the light beams from the light sources 12, 13, 14 are modulated by the optical modulators 22, 23, 24. For this purpose the optical modulators 22, 23, 24 are connected to an oscillator which provides the three distinct modulating frequencies f1, f2, f3.

Thus, in accordance with the teaching of the present invention, the individual spectral components are marked with the frequencies f1, f2, f3. The optical radiation falling on the single photoelectric receiver 18 thus consists of the three spectral components from the light sources 12, 13, 14 which have been modulated by the frequencies f1, f2 and f3 and possibly attenuated by gases flowing through the measuring section 11. An electronic processing circuit 32 receives the output signal from the single photoelectric receiver 18 and separates the individual signals from one another in dependence on the marking frequencies f1, f2 and f3 by filtering. Electrical signals which correspond to the attenuation of the individual spectral components from the light sources 12, 13 and 14 due to passage through the measuring section 11 are thus present at the output terminals 34, 35, 36.

The spectral component emitted by the light source 12 corresponds, by way of example, to a spectral component lying in the rotation-excitation bands of the gas carbon monoxide whereas the radiation emitted by the other two light sources 13, 14 has frequencies which are present in the rotation-excitation bands of two further gases such as $SO_2$ or $NO_x$. The apparatus of FIG. 1 is thus suitable for analysing three different gases. The number of gases to be analysed can be increased by using further spectral components and modulation frequencies.

Care should be taken that the spectral components emitted from the individual light sources or filters are only absorbed by one of the gases contained in the mixture.

Turning now to FIG. 2 there can be seen an arrangement in which a light beam emitted from an infra-red light source 12 is concentrated via a concave mirror 37 in the inlet slot of a polychromator 39. The light passes from the inlet slot 38 to a reflection grating 27 in the form of a concave holographic grating which produces spectral division of the incident light in the indicated manner. Three outlet slots 12', 13', 14' are arranged laterally spaced apart from one another at the output of the polychromator. Light in a quite specific narrow wavelength band around a specific basic wavelength thus emerges from each of the three outlet slots 12', 13', 14'. Narrow wave bands $\Delta\lambda_{oi}$ (i=1,2,...) based around the basic wavelengths $\lambda_{oi}$ are thus selected from the continuous spectrum of the infra-red light source 12. The outlet slots 12', 13', 14' of the polychromator 39 are so adjusted that they ovelap with disjoint regions of the absorption bands of the gases to be investigated. When using three outlet slots it is once again possible to analyse three gases present in the measuring section. The task of the polychromator 39 is only to effect an initial coarse spectral selection. The polychromator can accordingly be constructed to produce maximum light intensity.

The slots 12', 13' and 14' can each be regarded as a secondary light source which emits light with a specific spectral component.

The light emitted by the slots 12', 13', 14' is concentrated by lenses 40, 41, 42 which are only schematically illustrated, onto dichroic mirrors 15, 16 and 17 which unite the individual light beams leaving the polychromator 39 with one another. The so collimated light beams are colinearly deflected to the inlet of a two beam interferometer 25 which, in the present special case, is assumed to be a Michelson interferometer. In the usual manner the two beam interferometer consists of a partially transparent mirror 43 arranged at an angle of 45° and two plane reflecting mirrors 26, 43' arranged at right angles to one another.

In accordance with the invention a plane mirror, for example the mirror 26, is periodically moved to and fro in the direction of the double arrow x at a constant speed as shown in the diagram of FIG. 3. During a to and fro movement executed at a constant speed v the intensities of the individual spectral components $\lambda_{oi}$ (i=1, 2, ...) present in the incident light beam are modulated by the following frequencies:

$$f_{oi} = v \cdot (1/\lambda_{oi}) \text{ [Hz]}$$

Each of these modulation frequencies which lie in the low frequency region is uniquely associated with the frequency of the associated spectral component. It is however necessary to ensure that the speed v of the interferometer mirror 26 is constant to a high degree of precision.

The modulated light beam which emerges from the interferometer 25 passes through the measuring section 11 which can, for example, be formed by the interior of a chimney or flue.

At the end of the measuring section the light beam is concentrated by a concave mirror 44 onto a photodetector 18 the output signal of which is applied to the electronic processing circuit 32. This electronic processing circuit 32 is constructed as a low frequency spectral analyser of the same type as used with the embodiment of FIG. 1. The electronic processing circuit 32 once again contains narrow band filters f1, f2, f3 which are usefully regulable for the purpose of accurate adjustment. The integrated signal I ($\lambda_i$) at the outlet of each of the filters is proportional to the intensity of the individual light waves modulated by the frequencies f1, f2 and f3 and having wavelengths $\lambda_{01}$, $\lambda_{02}$ and $\lambda_{03}$. It is also possible to use an infra-red laser 12' with a multiple line spectrum in place of the polychromator 39, the lenses 40, 41, 42 and the mirrors 15, 16 and 17 in the manner illustrated in broken lines in FIG. 2. The multiple line laser should emit the three spectral components that are of interest.

Turning now to FIG. 5 there is shown an alternative embodiment which is similar to that of FIG. 2 and in which like parts are designated with the same reference numerals.

In the arrangement of FIG. 5 the polychromator 39 includes two further reflection mirrors 45, 46. The three spectral components required for the measurement are once again present at the outlet slots 12', 13', 14' and can be processed in the same way as for the embodiment of FIG. 2. The reflection grating is laid out in the present embodiment in the so-called "Ebert" arrangement.

In distinction to the embodiment of FIG. 2 the reflection grating 27 can also be periodically pivoted to and fro through an angle φ about an axis 47 standing at right angles to the plane of the drawing. This periodic pivotal movement of the reflection grating illustrated in FIG. 4 from which it can be seen that the reflection grating alternatively adopts the angular position φ1 and the angular position φ2 for equal periods of time.

So long as the reflection grating is in the angular position φ1 the light from the light source 12 is divided in accordance with the embodiment of FIG. 2; i.e. the three spectral components required for the measurement pass to the interferometer 25 and through the measurement section 11.

The angle φ2 of the reflection grating is now selected in such a way that spectral components which are not absorbed by any of the gases present in the measuring section reach the slots 12', 13', 14'. As a consequence, during the periods in which the reflection grating adopts the angle φ2, the light reaching the photoreceiver 18 through the measuring section 11 is not attenuated. The outlet signals appearing at the photoreceiver 18 during these periods can thus be used as reference values for the measurement signals.

In order to use these reference values in the evaluation the electronic processing circuit 32 of FIG. 5 is modified in the following way when compared with the embodiment of FIG. 2:

A square wave pulse generator 48 controls the position of the reflection grating in accordance with the diagram of FIG. 4. A change-over switch 49 is actuated in synchrony with the movement of the reflection grating 27. The change-over switch 49 selectively connects the output of the photoreceiver 18 to the low frequency spectral analyser with the filters 19, 20 and 21 or to a reference value forming circuit with the filters 50, 51, 52. The filters 50, 51, 52 are once again tuned to the modulation frequencies which are applied to the associated spectral components on their passage through the interferometer 25.

The connections between the square wave generator 48 and the reflection grating 27 and the change-over switch 49 are shown in chain dotted lines in FIG. 5 whereas the reference value forming circuit is illustrated simply in broken lines.

The outputs of the filters 19, 20, 21 and 50, 51, 52 are passed to quotient forming stages 53, 54, 55 in which the respective quotients between the measurement value and the reference value are formed. Normalized measurement signals, from which influences such as ageing of the lamp and contamination of the optics have been eliminated, thus appear at the outputs 34, 35 and 36.

The same circuit employing reference values could also be used in the embodiment of FIG. 2. The double arrow v at the concave holographic grating 27 of FIG. 2 indicates the possibility of carrying out a periodic pivotal movement of the grating in accordance with the diagram of FIG. 4.

FIG. 5 thus shows a differential spectrometer in which it is important that the wavelength selected by the outlet slots in the angular position 2 do not coincide with spectral components of the gases under investigation. The same applies to the use of interference filters and gradient density filters. The interference modulator 25 results in different frequencies $f_{iR}$ in the low frequency range being associated with the reference wavelengths $\lambda_{iR}$. The analysis of the signals delivered from the photoelectric receiver 18 to the electronic processing circuit basically consists of the formation of the following values by the quotient forming stages 53, 54, 55:

$$[I(\lambda_{iR}) - I(\lambda_{iO})]/I(\lambda_{iR})$$

The resulting values correspond to the concentration of the gases i in the measurement section 11. These values are independent of transmission losses through contamination of the optics, ageing of the lamp and absorption through any other gases which may be present such as water vapour-providing these gases behave in the same way with respect to absorption at the wavelengths $\lambda_{iO}$ and $\lambda_{iR}$.

In the embodiment of FIG. 6 the same reference numerals are once again used to designate parts which have counter parts in earlier embodiments.

Turning now specifically to FIG. 6 an arrangement is shown in which an apertured disk, of which only one half is shown, rotates in the outlet plane of the polychromator 39 about an axis of rotation 56. A series of slots are arranged on circular arcs of the disk at different radii r1, r2 and r3 with mark to space ratios of 1:1.

Small concave mirrors 57, 58 and 59 are arranged behind the slots 12', 13' and 14' respectively. The three concave mirrors 57, 58 and 59 have the same radius of curvature and are respectively spaced from their associated slots by a distance equal to this radius of curvature. The concave mirrors 57, 58 and 59 reflect the light beams emerging from the slots 12', 13' and 14' back on themselves. In this way the light is passed back via the mirrors 55, 56 and the reflection grating 27 to a beam divider 60 provided at the input side of the polychromator 39 between the entry slot and the deflecting mirror 45. The beam divider 60 concentrates the light beam onto a secondary outlet slot 61 and the light subsequently passes via a concave deflecting mirror 62 through the measurement section 11 onto the photoreceiver 18 which is again arranged at the other end of the measurement section. The electronic processing circuit 32 which is connected to the photoreceiver 18 is the same circuit that is used in the embodiment of FIG. 5. The embodiment of FIG. 6 also makes particular use of the square wave pulse generator 48 which switches the reflection grating 27 between the two angles φ1 and φ2 as shown in FIG. 4 and which connects the change-over switch 49 to the measuring filters 19, 20, 21 or to the reference filters 50, 51, 52 as appropriate.

It will be appreciated that two spectral components namely one measurement wavelength and one reference wavelength are associated with each of the circular rows of slots formed in the rotating aperture disk 28 at the radii r1, r2 and r3. As a result the three spectral components used for measurement purposes can readily be modulated at different frequencies simply by varying the number of slots in each of the three circular rows. The same applies to the three reference components. Clearly the widths of the slots of each of the individual rows affect the spectral resolution of the apparatus. In other words the width of the slot is a determining factor in controlling the band width of each of the spectral components. Clearly all wavelengths within the band width of any one spectral component will be modulated at the same frequency. This is however not disadvantageous if one is investigating gas components with broad absorption lines, or using a light source with several individual lines, particularly when compared with the multiplex advantage namely, the ability to investigate several gas components at the same time using only one photodetector.

The light beam is focussed onto the photoelectric receiver 18 after passing through the measurement section 11. The signal analysis takes place in the low frequency spectral analyser which is again included in the electronic processing circuit 32. As the band width of the low frequency spectral analyser does not affect the spectral resolution it is advantageous to provide the low frequency spectral analyser with a fairly broad band width in order to compensate for fluctuations in the speed of rotation of the apertured disk 28. When using synchronized demodulators the reference frequency can also be picked up from the apertured disk which automatically takes account of fluctuations in the rotational speed of the disk.

We claim:

1. In an apparatus for analysing by spectral absorption a gaseous mixture containing several molecular gases, said apparatus comprising one or more radiation sources for generating spectral components each having a wavelength characteristic of a respective vibrational-rotational-excitation band for one of said gases, modulator means for modulating each of said spectral components with a uniquely associated marking frequency, means for jointly directing said spectral components in the form of a measuring beam through said gaseous mixture onto a photoreceiver, and an evaluation circuit including electronic filter means tuned to each of said marking frequencies connected to receive signals from said photoreceiver and to deliver signals proportional to the intensity of the associated spectral component, the improvement wherein said photoreceiver is the photoreceiver of a two beam interferometer having a movable mirror, wherein means are provided for directing said spectral components from each said radiation source onto said movable mirror in the form of a collimated beam of light, and wherein means are provided for moving said movable mirror to and fro along said beam of light over at least a few wavelengths to modulate said spectral components at said marking frequencies.

2. An apparatus in accordance with claim 1 wherein said means for moving said movable mirror is adapted to move said mirror at a constant speed during each phase of said to and fro movement.

3. An apparatus in accordance with claim 1 or 2 wherein said two beam interferometer is a Michelson interferometer.

4. An apparatus in accordance with claim 1 in which said spectral components are generated by a single radiation source.

5. An apparatus in accordance with claim 1 in which said spectral components are generated by a plurality of secondary light sources formed by the spectral division of a single radiation beam containing all spectral components required for the analysis.

6. An apparatus in accordance with claim 5 in which said spectral division is formed by a reflection grating and a plurality of slots, said grating concentrating each of said spectral components into a corresponding slot.

7. An apparatus in accordance with claim 6 in which means are provided for moving said slots in a periodic modulating movement at said marking frequencies.

8. An apparatus in accordance with claim 5, 6, or 7 in which said reflection grating is periodically pivotable between two positions, and a spectral measuring component is generated at said slots when said grating is in one of said positions, and a spectral reference component is generated at said slots when said grating is in the other of said positions.

* * * * *